United States Patent [19]

Namekawa

[11] Patent Number: 4,799,490

[45] Date of Patent: Jan. 24, 1989

[54] DOPPLER ULTRASONIC DIAGNOSTIC APPARATUS

[75] Inventor: Kouroku Namekawa, Tokyo, Japan

[73] Assignee: Aloka Co., Ltd., Tokyo, Japan

[21] Appl. No.: 20,439

[22] Filed: Mar. 2, 1987

[30] Foreign Application Priority Data

Mar. 4, 1986 [JP] Japan ................................ 61-045291
Mar. 4, 1986 [JP] Japan ................................ 61-045292

[51] Int. Cl.$^4$ ............................................. A61B 10/00
[52] U.S. Cl. ............................. 128/661.09; 73/861.25
[58] Field of Search .......................... 128/663, 661.09; 73/861.25; 367/90, 99

[56] References Cited

U.S. PATENT DOCUMENTS

| | | | |
|---|---|---|---|
| 3,940,731 | 2/1976 | Cooper et al. ................... | 128/663 X |
| 4,255,977 | 3/1981 | Newhouse et al. .............. | 128/663 X |
| 4,320,765 | 3/1982 | Cathignol et al. ................ | 128/663 |
| 4,622,977 | 11/1986 | Namekawa et al. ............... | 128/663 |

Primary Examiner—Francis J. Jaworski
Attorney, Agent, or Firm—Koda and Androlia

[57] ABSTRACT

A Doppler ultrasonic-diagnostic apparatus for measuring or displaying the velocity information of moving members within an organism by transmitting and receiving ultrasonic waves is used for ultrasonic diagnosis in the medical field and the like.

The apparatus is composed of a transmission circuitry for producing two ultrasonic waves having different repetition periods and outputting an ultrasonic wave after change-over between them; a velocity calculating means for calculating the velocities of moving reflective members on the basis of the received Doppler signals from the two ultrasonic waves, for example, a velocity calculator or an autocorrelator for obtaining the autocorrelation of a received signal after converting it to a complex signal; a memory for storing the velocity information signals obtained by the velocity calculating means; and other calculating means.

The velocity of the moving reflective members is obtained by calculating the difference between or the sum of the two kinds of velocity signals, or calculating the conjugate product or the complex product of the two kinds of velocity signals. The present invention makes it easy to obtain accurate velocity information by an apparatus having a simple structure.

4 Claims, 3 Drawing Sheets

DOPPLER ULTRASONIC DIAGNOSTIC APPARATUS

BACKGROUND OF THE INVENTION

1. Field of the Invention

The present invention relates to a Doppler ultrasonic diagnostic apparatus and, more particularly, to a Doppler ultrasonic diagnostic apparatus which is capable of detecting and measuring the velocity of moving reflective members and accurately displaying the movement within an organism to be examined.

2. Description of the Prior Art

Doppler pulse devices are widely used wherein an ultrasonic pulse beam is transmitted into reflective members at a fixed repetition frequency, the reflected waves from the reflective members are received, and the distance to the reflective member is measured by comparing the time difference between the transmitted signals and the received signals and at the same time the velocity of movement of the reflective members is detected and measured by detecting changes in the frequency of the received signal.

Generally, the repetition frequency of the pulse beam is selected in accordance with the distance to the reflective member. In the case of measuring reflective members within an organism which is distantly located, however, if the frequency selected is high as compared with the repetition frequency determined on the basis of the distance to the reflective members, an aliasing echo is produced which indicates that the reflective members are situated closer than the actual position, as is well known, and this makes discrimination of the distance difficult.

A similar phenomenon is seen in the case of measuring the velocity of moving reflective members. If the repetition frequency selected is low as compared with the Doppler frequency arising from the velocity of the reflective members, an aliasing echo results in a low frequency, thereby making discrimination of the velocity difficult.

In order to measure both distance and velocity without production of aliasing echo, it is known that the relationship between a maximum Doppler frequency $f_{dmax}$ and pulse repetition frequency $f_r$ must conform to $f_{dmax}=f_r/2$ in the case of a device which is capable of detecting not only absolute velocity but also whether it is positive or negative, and $f_{dmax}=f_r$ in the case of a device which detects and measures only the absolute velocity.

In a device which is capable of determining whether velocity is positive or negative, the following relationship holds:

$$f_{dmax}=(2V_{max}/c) \cdot f_0 = f_r/2$$

($f_0$: ultrasonic pulse beam frequency, $V_{max}$ maximum velocity, c: sound velocity).

From this formula, the maximum measurable velocity $V_{max}$ is $V_{max}=(f_r/2) \cdot c/(2f_0)$.

The maximum distance to the reflective member $R_{max}$ which can unambiguously be determined is given by:

$$R_{max}=c \; T/2 = c/(2f_r)$$

where, $T=1/f_r$ is the pulse repetition interval.

However, as is obvious from the above formulas, such a device suffers from the problem that if the pulse repetition frequency $f_r$ is increased in order to increase the maximum measurable velocity $V_{max}$, there is a decrease in the maximum distance $R_{max}$ at which the moving reflective members can be measured without the production of aliasing echo, thereby making it impossible to measure rapidly moving reflective members from a long distance.

Combining $V_{max}$ and $R_{max}$ gives the following relationship:

$$V_{max} R_{max} = c^2/(8 \cdot f_0)$$

As is obvious from the above formula, another problem is that if a low ultrasonic beam frequency $f_o$ is selected, not only is it difficult to produce a transmission wave with a narrow pulse width but also it is impossible to form a finely focussed beam, resulting in a decrease in the distance resolution and the directional resolution, thus rendering it impossible to simultaneously establish the distance to and the velocity of a distantly located rapidly moving reflective members.

SUMMARY OF THE INVENTION

Accordingly, it is an object of the present invention to eliminate the above-described problems in the prior art and to provide a Doppler ultrasonic diagnostic apparatus which enables the velocity of reflective members in a wide range of from a low speed to a high speed, in particular, the velocity of rapidly moving reflective members which are located at a long distance to be obtained with good accuracy.

To achieve this aim, the present invention provides in one aspect a Doppler ultrasonic diagnostic apparatus which is composed of: a transmission circuitry for producing two ultrasonic waves having different repetition periods in the same direction and outputting an ultrasonic wave after change-over between them; a velocity calculator for calculating the velocities of moving reflective members from the respective received Doppler signals of the two ultrasonic waves; a memory for storing a first velocity signal obtained by the velocity calculator on the basis of the ultrasonic wave which has been transmitted first in that direction; and an adder-subtracter for calculating the sum of or the difference between a second velocity signal obtained by the velocity calculator on the basis of the ultrasonic wave transmitted later in that direction and the first velocity signal.

According to the above-described structure, two ultrasonic waves having different repetition periods are first output from the same probe, and these two ultrasonic waves are successively transmitted in the same direction into an organism to be examined. The respective velocities of the ultrasonic waves are calculated by the velocity calculator on the basis of the received Doppler signals of the reflected echoes, and the first velocity signal obtained from the ultrasonic wave which has been transmitted first is stored in the memory.

The second velocity signal obtained from the ultrasonic wave which is transmitted later is directly input to the adder-subtracter, wherein the difference between or the sum of the first and second velocity signals is calculated.

The velocity signal includes a deviation of the repetition frequency from the carrier frequency, namely, changes in velocity, and it is possible to accurately obtain the velocity of rapidly moving reflective members from a difference velocity signal and the velocity of slowly moving reflective members from a sum velocity signal.

In another aspect of the present invention, a Doppler ultrasonic diagnostic apparatus is provided which is composed of: a transmission circuitry for producing ultrasonic waves having two different repetition periods in the same direction and outputting an ultrasonic wave after change-over between them; a complex signal converter for mixing and detecting a Doppler signal obtained from an organism to be examined and a complex reference wave and converting them to a complex signal; an autocorrelator for calculating the autocorrelation of the complex signal by providing a delay time which is an integer multiple of a repetition period; a memory for storing a first autocorrelation signal obtained by the autocorrelator on the basis of the ultrasonic wave which has been transmitted first in that direction; and a velocity processor for obtaining the velocity of moving reflective members by calculating the conjugate product or the complex product of a second autocorrelation signal obtained by the autocorrelator on the basis of the ultrasonic wave transmitted later in that direction and the first autocorrelation signal, thereby accurately obtaining the velocity of the moving reflective members.

According to the second aspect of the present invention, two ultrasonic waves are successively transmitted in the same direction into the organism, in the same way as in the first aspect of the invention, but the received Doppler signal of the reflected echo obtained from the organism is converted to a complex signal and is thereafter supplied to the autocorrelator. The autocorrelator produces two autocorrelation signals; a first autocorrelation signal being obtained from the ultrasonic wave which has been transmitted first of the two ultrasonic waves having repetition periods, while a second autocorrelation signal is obtained from the ultrasonic wave transmitted later.

On the basis of these autocorrelation signals, the complex signals are converted to Doppler signals which are substantially obtained from ultrasonic waves of a short or long repetition period. That is, the first autocorrelation signal is stored in the memory and when the second correlation signal is output, the conjugate product or the complex product of the first and second autocorrelation signals is obtained, thereby the velocity being calculated.

The argument of the conjugate product is the shift of a frequency of a Doppler signal substantially obtained when an ultrasonic having a short period (the repetition frequency $f_r$ is high) is transmitted to the organism, and the argument of the complex product is the shift of a frequency of a Doppler signal obtained when an ultrasonic wave having a long repetition period (the repetition frequency $f_r$ is low) is transmitted. Therefore, as is clear from the above-described formula: the maximum velocity $V=f_r/(2f_0 \cdot K)$, it is possible to accurately obtain the velocity of rapidly moving reflective members from the conjugate product and that of slowly moving reflective members from the complex product.

The above and other objects, features and advantages of the present invention will become clear from the following description of the preferred embodiments thereof, taken in conjunction with the accompanying drawings.

DESCRIPTION OF THE PREFERRED EMBODIMENTS

First Embodiment

A first embodiment of the present invention will be explained hereinunder with reference to FIG. 1.

Figure 1:
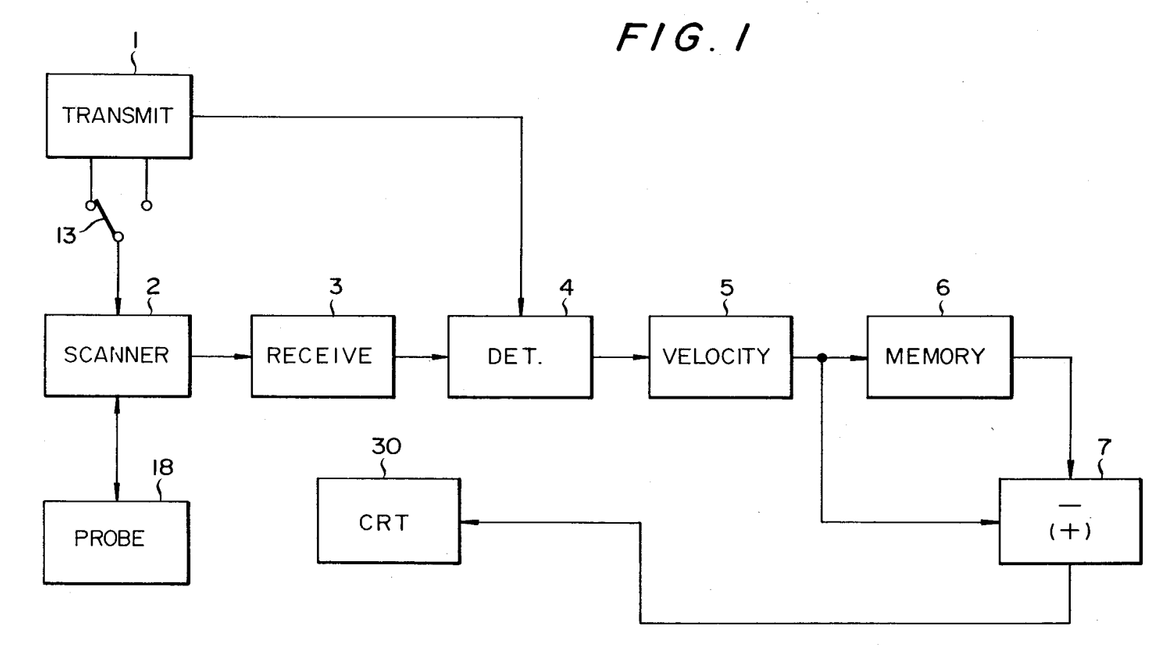
FIG. 1 is a circuit diagram of a first embodiment of a Doppler ultrasonic diagnostic apparatus according to the present invention.

FIG. 1 shows the structure of the circuit of a Doppler ultrasonic diagnostic apparatus, which is provided with a transmitter 1 for transmitting pulses of a fixed repetition frequency, and the output of the transmitter 1 is supplied to an electronic scanner 2.

The present invention is characterized in that two ultrasonic waves having different repetition periods are transmitted to the same direction. For this purpose, a transmission period switch 13 is provided in order to supply two transmission signals having different repetition periods to the electronic scanner 2. The electronic scanner 2, if it performs sector scanning, controls the deflection angle of the beam. Control of the electronic scanner 2 excites a probe 18, thereby producing two ultrasonic pulse beams having different cycles in a given direction. Thus, the transmitter 1, the transmission period switch 13, the electronic scanner 2 and the probe 18 in combination constitute a transmission circuitry.

The probe 18 is brought into contact with the surface of an organism, and ultrasonic waves are transmitted into the organism. The reflected echoes from the reflective members are received by the same probe 18 and are supplied to a receiver 3 through the electronic scanner 2. The receiver 3 amplifies the received ultrasonic signal and outputs it to a detector 4. The detector 4 mixes and detects the received signal and the reference wave which has a frequency of an integer multiple of the repetition frequency and is output from the transmitter 1.

The output of the detector 4 is supplied to a velocity calculator 5, in which the received signal which is an analog signal is converted to a digital signal, and thereafter the velocity is calculated.

The velocity can be obtained in various methods. For example, a received Doppler signal is converted to a complex signal and from the argument of the complex signal the velocity is obtained.

That is, if a complex signal Z is represented by the formula $Z=x+iy$, the argument $\theta$ is obtained from the following formula:

$$\theta = \tan^{-1}(y/x) \qquad (1)$$

The argument represents the shift of a frequency of the carrier, namely, a Doppler frequency, and if the Doppler frequency is fd and the repetition period is T, the following relationship holds:

$$f_d = \theta/2\pi T \qquad (2)$$

and thus, the velocity of moving reflective members is obtained from the argument $\theta$ of the complex signal.

In the present invention, two ultrasonic waves having different repetition periods are transmitted in the same direction into an organism, and the velocity of moving reflective member in the range of a low speed to a high speed is obtained on the basis of the two ultrasonic waves, as described above. In the first embodiment, the accurate velocity of moving reflective members is obtained from the two velocity values obtained by the velocity calculator 5.

For this purpose, this embodiment is provided with a memory for storing all the first velocity signals on the ultrasonic beam axis obtained from the ultrasonic waves which have been first transmitted, a line memory 6 in this embodiment, and an adder-subtracter 7 for successively calculating the sum of or the difference between a second velocity signal obtained from the ultrasonic wave which is transmitted later and the first velocity signal. The velocity of the moving reflective members obtained by the adder-subtracter 7 is displayed on a CRT display 30. The CRT display 30 displays the mode of the organism as M-mode or B-mode, and velocity information is displayed together therewith.

The operation of the first embodiment having the above-described structure will now be explained.

Of the two velocity signals obtained by transmitting the two ultrasonic waves having different repetition periods in the same direction, the first velocity signal which is output first is supplied to and stored in the line memory 6, and the second velocity signal which is output later is supplied to the adder-subtracter 7. The adder-subtracter 7 reads out the first velocity signal from the line memory 6 and calculates the difference between the two velocity signals.

If it is assumed that $\theta$ obtained by the formula (1) is a velocity signal and the first velocity signal obtained from the ultrasonic wave which has been first transmitted is $\theta_1$, the second velocity signal obtained from the ultrasonic wave which is transmitted later being $\theta_2$, $\theta_1 - \theta_2$ is calculated in the following formula:

$$\theta_1 - \theta_2 = 2\pi f_d(T_1 - T_2) = 2\pi f_d \Delta T \quad (3)$$

wherein $T_1$ represents the repetition period of the ultrasonic wave which has been transmitted first and $T_2$ the repetition period of the ultrasonic wave which is transmitted later. The argument $\theta_1 - \theta_2$ obtained from the formula (3) is a velocity signal obtained when the ultrasonic wave having the repetition period $\Delta T$ is transmitted. Since the repetition period $\Delta T$ is $T_1 - T_2$, the argument $\theta_1 - \theta_2$ turns out to be the same as a Doppler signal obtained when the ultrasonic wave having a short repetition period (high repetition frequency $f_r$) is transmitted.

Accordingly, for example, if the repetition period $T_1 = 250$ $\mu$s (the repetition frequency $f_r 1 = 4$ KHz) and the repetition period $T_2 = 200$ $\mu$s (the repetition frequency $f_r 2 = 5$ KHz), $\Delta T$ equals 50 $\mu$s (the repetition frequency $f_r = 20$ KHz). As a result, the maximum measurable Doppler frequency in this case is 20 KHz $\div 2 = 10$ KHz, which is four times the maximum Doppler frequency 2.5 KHz ($= 5$ KHz $\div 2$) obtained when the repetition period is $T_2$.

In this manner, high-speed measurement is enabled by calculating the velocity signals obtained from the two ultrasonic waves having different frequency periods, and it is possible to convert a Doppler signal to a desired signal without almost any change in the maximum measuring depth by selecting appropriate values for the repetition periods $T_1$ and $T_2$.

In the first embodiment, it is also possible to accurately obtain the velocity in a low-speed range by actuating the adder-subtracter 7 as an adder.

The formula (3) is represented in this case as follows:

$$\theta_1 + \theta_2 = 2\pi f_d (T_1 + T_2) = 2\pi f_d \Delta T \quad (4)$$

The argument is equivalent to a Doppler signal obtained when the ultrasonic wave having a long repetition period (low repetition frequency $f_r$), and since the velocity value is enlarged in a predetermined speed range when the Doppler frequency $f_d$ is low, the low speed of the moving reflective member is detected with high accuracy.

As has been explained, according to the first embodiment, since two ultrasonic waves having different repetition periods are transmitted in the same direction into an organism so that the sum of or the difference between the two velocity signals obtained from the respective ultrasonic waves is obtained, it is possible to convert the sum or the difference into a signal which corresponds to a Doppler signal containing a velocity signal in a wide range of from a high speed to a low speed, thereby making it easy to obtain the accurate velocity of a moving reflective member.

Second Embodiment

Figure 2:
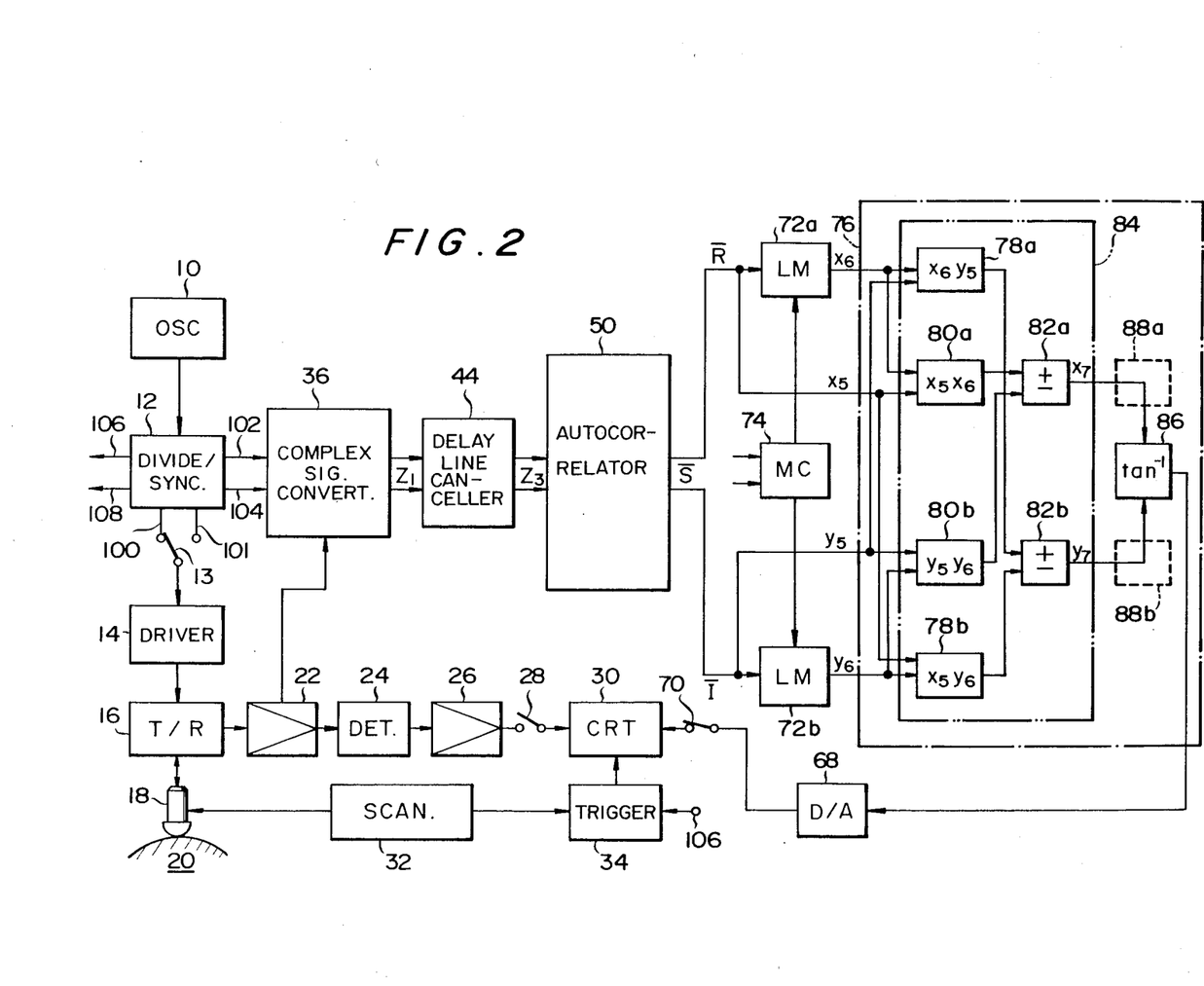
FIG. 2 is a circuit diagram of a second embodiment of a Doppler ultrasonic diagnostic apparatus according to the present invention.
Figure 3:
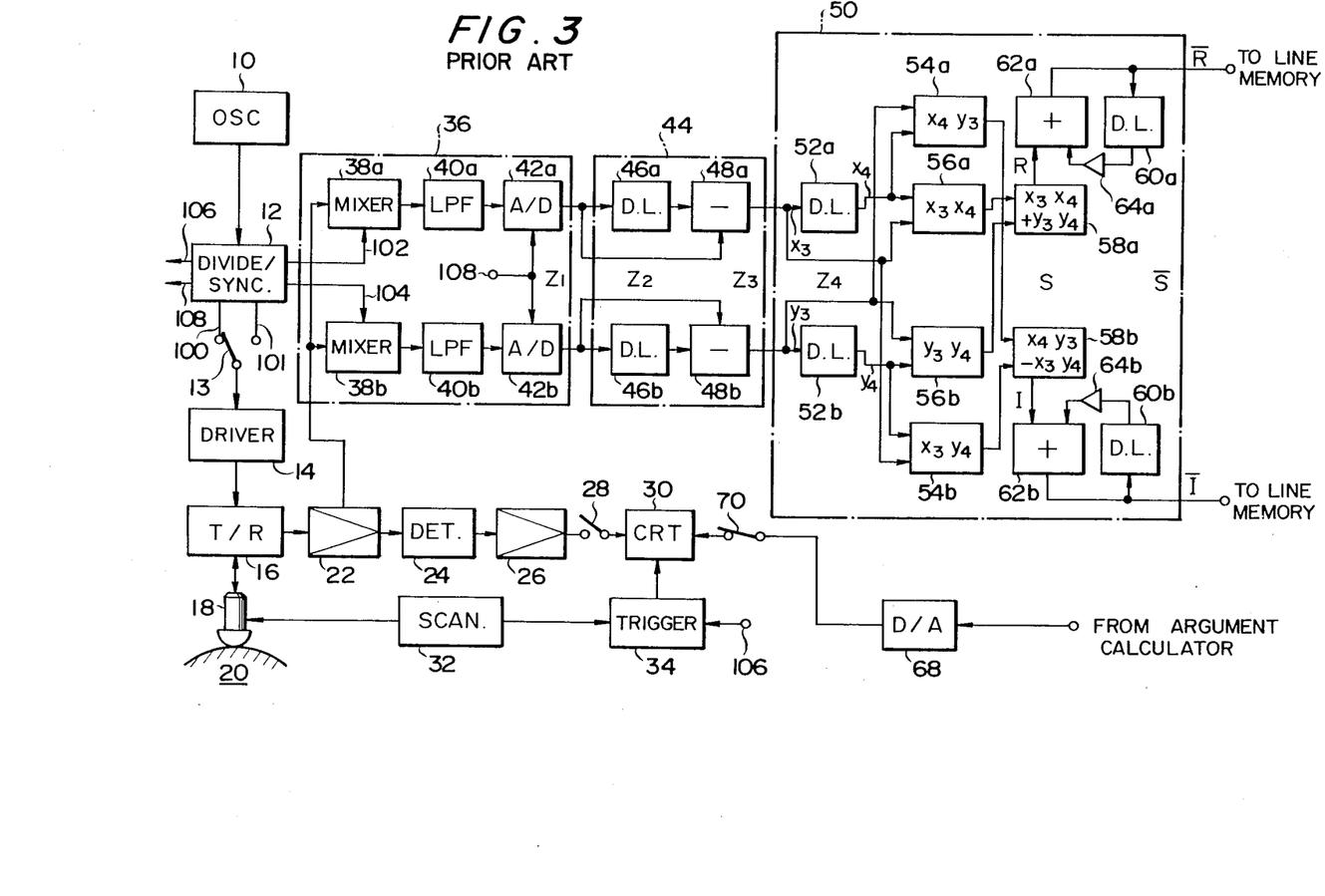
FIG. 3 is a block diagram of the structure of the circuit for obtaining autocorrelation signals on the second embodiment.

A second embodiment of the present invention in which the velocity of a moving reflective member is obtained by an autocorrelation method will here be explained.

FIGS. 2 and 3 show the structure of the circuit of a Doppler ultrasonic diagnostic apparatus. Calculation of autocorrelation signals will first be explained with reference to FIG. 3.

Calculation of Autocorrelation Signals

Referring to FIG. 3, the output of a crystal oscillator 10 is supplied to a frequency divider and sync generator 12, from which various output signals of a desired frequency are obtained.

The second embodiment in which two ultrasonic waves having different repetition periods are also transmitted is provided with the transmission period switch 13, and the transmission circuitry is composed of the crystal oscillator 10, the frequency divider and sync generator 12, the transmission period switch 13, a driver 14, a duplexer 16 and the probe 18. The output signal of the frequency divider and sync generator 12 outputs two transmission repetition frequency signals 100, 101 for transmitting ultrasonic pulse waves and outputs, in addition, complex reference signals 102, 104 for complex conversion, a sweep synchronizing signal 106 for use in displaying the results of the ultrasonic diagnosis, and a clock signal 108 for synchronizing various sections of the apparatus.

In the second embodiment, the complex reference signals 102, 104 have frequencies which are integer multiples of the transmission repetition frequency signals 101, 102, respectively, and are phase-shifted from one another, by 90 degrees, in this embodiment, so as to be in a complex relationship.

The transmission signals 100, 101 are supplied to the probe 18 through the driver 14 and the duplexer 16, and excite the probe 18 so as to transmit two ultrasonic pulse beams having different repetition periods into a specimen 20.

The echoes reflected from the specimen 20 are converted into electrical signals by the probe 18 and are forwarded through the duplexer 16 to a high frequency amplifier 22 by which they are amplified to a prescribed degree, and one of the outputs is supplied to the display section as an ordinary B-mode or M-mode display signal.

The output signal for carrying out an ordinary B-mode or M-mode display is supplied from a detector 24 and a video amplifier 26 to the CRT display 30 through a switch 28, thereby modulating the brightness of the screen.

The probe 18 is provided with a scanning controller 32 for angularly deflecting the ultrasonic pulse beam either mechanically or electrically, so as to periodically scan the specimen 20, or for halting the scanning operation at a desired deflection angle. The scanning position signal from the scanning controller 32 and the sweep synchronizing signal 106 obtained from the frequency divider and sync generator 12 are supplied to a sweep trigger pulse generator 34 in order to sweep-control the CRT display 30.

The other output of the high frequency amplifier 22 is subjected to the calculation of autocorrelation in accordance with the present invention. The received Doppler receiving signal which is output from the high frequency amplifier 22 is first supplied to a complex signal converter 36 to be converted to a complex signal.

In this embodiment, the complex signal converter 36 is provided with a pair of mixers 38a, 38b, each of which includes a phase detector. The received signal is mixed with the complex reference signals 102, 104 in the respective mixers 38. Since the complex reference signals 102, 104 are in a complex relationship, namely, since they are 90 degree out of phase, as described above, it is possible to output the complex signals which correspond to the high frequency signal from the mixers 38. More precisely, as a result of mixing and detecting operation of the received signal and the respective complex reference signals, each of the mixers 38 outputs two signals, one having a frequency equal to the sum of the frequencies of the input received signal and the complex reference signal, an the other having a frequency equal to the difference between their frequencies. Both signals are supplied to low pass filters 40a, 40b, which pass only the respective difference frequency component.

In the mixing and detecting operation carried out by the mixers 38, the complex reference signals 102, 104 are single-frequency continuous waves, whereas the other input signal, namely, the received signal is a pulse wave including Doppler information. As a result, the outputs from the low pass filters 40 include a large number of spectral components. The complex conversion will now be explained through the use of conversion formulas.

The complex reference signal 102 has a frequency f0 which is an integer multiple of the transmission repetition frequency $f_r$, and if the amplitude of this complex frequency signal 102 is taken as 1, the complex reference signal 102 is represented as the following sine wave voltage signal:

$$\sin 2\pi f_0 t \qquad (5)$$

On the other hand, if the transmission frequency is taken as $f_0$, the signal received by the probe 18 is expressed as $$\sin (2\pi f_0 t + 2\pi f_d t) \qquad (6)$$

wherein fd is the Doppler shift frequency.

Although this received signal generally includes the spectrum $$\sin \{2\pi(f_0 \pm {}^n f_r) t + 2\pi f_d \cdot (1 \pm n f_r / f_0) t\}$$

(wherein $f_r$ is the transmission repetition frequency and n is a natural number such as 0, 1, 2 ... ), only the spectrum shown in the case in which n=0, namely, the spectrum represented by formula (2) will be explained hereinunder for the purpose of simplifying the explanation.

Since the product of the complex reference signal 102 and the received signal is obtained in the mixer 38a, the output expressed by the following formula is derived which is equal to twice the product of formulas (5) and (6):

$$\cos 2\pi f_d t - \cos (4\pi f_0 t + 2\pi f_d t)$$

Since the frequency of $2f_0 + f_d$ is eliminated from this output by the low pass filter 40a, the output signal is expressed as $$\cos 2\pi f_d t \qquad (7)$$

On the other hand, the other complex reference signal 104 is out of phase by 90 degrees with respect to the signal 102, it is expressed as the following cosine voltage signal:

$$\cos 2\pi f_0 t \qquad (8)$$

and is converted into the following signal after being mixed and detected in the mixer 38b and by the filtering operation of the low pass filter 40b:

$$\sin 2\pi f_d t \qquad (9)$$

thus producing a complex signal having a real component represented by formula (7) and an imaginary component represented by formula (9). These signals are represented by the following formula:

$$Z_1 = \cos 2\pi f_d t + j\sin 2\pi f d t \qquad (10)$$

The signals $Z_1$ thus obtained by complex conversion are then converted to digital signals by A/D converters 42a, 42b, and thereafter they are forwarded to a complex delay-line canceller 44. The clock signal 108 is supplied to the A/D converters 42 for sampling.

Since the second embodiment is provided with the complex delay-line canceller 44, it is possible to eliminate the portions of the signal received from the stationary or slow moving members within the organism and to obtain velocity signals of only the moving portions, thereby greatly improving the quality of the video signal.

The complex delay-line canceller 44 has a pair of delay lines 46a, 46b each of which has a delay time equal to one period (T) of the repetition signal. These delay lines 46a, 46b may be constituted, for example, by a memory or a shift register which consists of the same number of memory elements as the number of clock pulses contained in one period. Subtracters 48a, 48b are connected to the delay lines 46. The subtracters 48 successively compare the inputs of the delay lines 46 (i.e. the signals during the current period) with the outputs thereof (i.e. the signals during the preceding period) at the same depth and calculate the difference between the signals during one period. Therefore, the echo signals from the stationary or slowly moving member exhibit little or no difference between one period, so that the output of the subtracters 48 approaches zero, while the output of a rapidly moving member, for example, blood flow signals are detected as a large value, so that it is possible to suppress the reflected signal from the stationary or slowly moving object, namely, clutter.

The operation of the complex delay-line canceller 44 will be explained in the following with reference to the following formulas. Although digital signals are input to the delay-line canceller 44 in FIG. 3, the following explanation will be made on the basis of the analog signals represented by formula (10) for the purpose of simplifying the explanation. If the inputs $Z_1$ of the delay-line canceller 44 are represented by formula (10), the output $Z_2$ delayed by one period is represented by the following formula:

$$Z_2 = \cos 2\pi f_d(t-T) + j\sin 2\pi f_d(t-T) \quad (11)$$

As a result, the difference outputs of the subtracters 48 are $$Z_3 = Z_1 - Z_2 = -2\sin 2\pi f_d(T/2)\cdot \sin 2\pi f_d \{t-(T/2)\} + j2 \sin 2\pi f_d(T/2)\cdot \cos 2\pi f_d\{t-(T/2)\}$$

If the difference output $Z_3$ is expressed by $$Z_3 = x_3 + jy_3$$

$x_3$, $y_3$ are expressed by the following formulas;

$$x_3 = -2 \sin 2\pi f_d (T/2)\cdot \sin 2\pi f_d \{t-(T/2)\} \quad (12)$$

$$y_3 = 2 \sin 2\pi f_d(T/2)\cdot \cos 2\pi f_d\{t-(T/2)\} \quad (13)$$

Thus, $x_3$, $y_3$ are output from the subtracters 48a, 48b, respectively.

The complex signals from which the low velocity signal components have been eliminated in the above-described way are then processed by an autocorrelator 50 in order to obtain the autocorrelation of the signals $Z_3$ having a delay of T.

The input signals $Z_3$ are delayed by one period by delay-lines 52a, 52b to produce signals $Z_4$. The output $Z_4$ is represented by the following formula:

$$Z_4 = x_4 + jy_4$$

$$x_4 = -2 \sin 2\pi f_d (T/2)\cdot \sin 2\pi f_d\{t-(3T/2)\} \quad (14)$$

$$y_4 = 2 \sin 2\pi f_d (T/2)\cdot \cos 2\pi f_d\{t-(3T/2)\} \quad (15)$$

The conjugate signal $Z_4^*$ of the signal $Z_4$ is represented by $Z_4^* = x_4 - jy_4$, and the conjugate product of $Z_3$ and $Z_4^*$ is obtained by the following formula, thereby calculating the autocorrelation:

$$Z_3 Z_4^* = (x_3 + jy_3)(x_4 - jy_4) = x_3 x_4 + y_3 y_4 + j(x_4 y_3 - x_3 y_4)$$

In order to obtain this autocorrelation, the autocorrelator 50 is provided with four multipliers 54a, 54b, 55a and 56b, and two adder-subtracters 58a, 58b.

If the output of the adder-subtracter 58b is R, the following formula is obtained from formulas (12), (13), (14) and (15):

$$R = x_3 x_4 + y_3 y_4 = 4\sin^2 2\pi f_d\cdot (T/2)\cos 2\pi f_d T \quad (16)$$

If the output of the adder-subtracter 58b is I, the following formula is obtained in the same way:

$$I = x_4 y_3 - x_3 y_4 = 4 \sin^2 2\pi f_d\cdot(T/2)\sin 2\pi f_d T \quad (17)$$

By combining the outputs from both adder-subtracters 58, the autocorrelation signal is expressed as follows:

$$S = R + jI \quad (18)$$

Since this output S includes the variable signal components and the noise component produced from the apparatus, it is averaged by an averaging circuit in order to eliminate such noise component. The average is expressed by $\bar{S} = \bar{R} + j\bar{I}$, whereby the autocorrelation is calculated.

In the average circuit, the operation of adding the outputs delayed by one period by delay lines 60a, 60b to the inputs for the current period by the adders 62a, 62b, and feeding back the outputs obtained to the delay lines 60 is repeated. If a digital circuit is used for this addition, the average value is obtained merely by outputting the zone bits of the added output. However, if this operation is simply repeated, the magnitude of the output successively increases with an increase in the numbers of additions, until at last saturation is reached. To prevent this, this embodiment is provided with weighting circuits 64a, 64b for attenuating the outputs before adding them to the inputs. More specifically, if the amount of attenuation is defined as $\alpha$, the signal for, for example, 10 periods earlier than the current period is attenuated by a factor of $\alpha^{10}$ relative to the signal for the current period before the former signal is added to the latter signal. Therefore, the effect on the output is made small, so that an averaging effect like that of a low pass filter or a running average circuit can be obtained. Moreover, it is possible to adjust the degree of averaging by changing the amount of weighting by the weighting circuits 64.

As described above, in the second embodiment, the autocorrelations of the complex signals are obtained by obtaining the conjugate product, and it is possible to obtain the velocity by obtaining the argument $\theta$ of the autocorrelation outputs $\bar{S}$. The argument $\theta$ is obtained from formulas (16) and (17) as follows:

$$\theta = \tan^{-1}(I/R) = 2\pi f_d T \quad (19)$$

As a result, it is very easy to obtain the Doppler shift frequency $\bar{f}_d$ from the argument $\theta$ as follows:

$$f_d = \theta/2\pi T \quad (20)$$

Although the autocorrelations are obtained from the conjugate product of the complex signals in the above explanation, it is also possible to obtain them from the complex product of the complex signals. According to the complex product, it is possible to obtain the velocity of moving reflective members at a short distance with high accuracy.

Velocity Processing in the Second Embodiment

As described above, the second embodiment is characterized in that two ultrasonic waves having different repetition periods are transmitted in the same direction into an organism, and the accurate velocity is obtained from the conjugate product or the complex product of the autocorrelation signal of a Doppler signal thereby obtained. For this purpose, the second embodiment is provided with line memories 72a, 72b for storing the first autocorrelation signals obtained from the transmitted ultrasonic wave which has been transmitted first, and a velocity processor 76 for calculating the velocity of moving reflective members from a second autocorrelation signal obtained from the ultrasonic wave which is transmitted later and the first autocorrelation signal, in addition to the above-described structure such as the autocorrelator 50.

The velocity processor 76 is composed of a complex multiplier 84 consisting of multipliers 78, 80 and adder-subtracters 82, and an argument calculator 86. The line memories 72 are provided for the purpose of delaying the first autocorrelation signal by a predetermined time in order to simultaneously compare the second autocorrelation signal and the first correlation signal. Various delay lines are usable in place of the line memories so long as they have the above-described function.

The second embodiment has the above-described structure. Velocity processing based on the conjugate product or the complex product will here be explained.

The outputs $\bar{R}$, $\bar{I}$ of the autocorrelator 50 are expressed by the following formulas on the assumption that the absolute value of the autocorrelation is $|S|$, and they are supplied to the line memories 72a, 72b, respectively.

$$R = |S| \cos \theta \quad (21)$$

$$I = |S| \sin \theta \quad (22)$$

The outputs R and I are the final values of the autocorrelator 50 and the average values obtained by transmitting ultrasonic pulses several times in a given direction. The argument $\theta$ is a signal which indicates individual item of velocity information obtained from an ultrasonic wave having a different period.

The velocity of moving reflective members is obtained on the basis of two autocorrelation signals obtained from two ultrasonic waves having different repetition periods. The first autocorrelation signal obtained from the ultrasonic wave which has first been transmitted is stored in the line memories 72. In the first autocorrelation signal the signal $\bar{R}$ is stored in the line memory 72a, while the signal $\bar{I}$ is stored in the line memory 72b. They are written into or read out of the memories by a memory controller 74 to which a clock pulse and a scanning address signal are supplied.

The second autocorrelation signal obtained from the ultrasonic wave which is transmitted later is directly supplied to the complex multiplier 84 of the velocity processor 76, not through the line memories 72. If the adder-subtracter 82a in the complex multiplier 84 is operated as an adder, and the adder-subtracter 82b as a subtracter, the conjugate product of the first and second autocorrelation signals is calculated.

The conjugate product means the product of the conjugate complex of one of the two autocorrelation signals and the complex number of the other autocorrelation signal. Therefore, the complex multiplier 84 calculates the following formula:

$$(\bar{R}_1 + j\bar{I}_1)(\bar{R}_2 - j\bar{I}_2) \quad (23)$$
$$= \bar{R}_1\bar{R}_2 - \bar{I}_1\bar{I}_2 + j(\bar{I}_1\bar{R}_2 - \bar{R}_1\bar{I}_2)$$
$$= x_7 + jy_7$$

$\bar{R}_1$, $\bar{I}_1$ are first autocorrelation signal components and $\bar{R}_2$, $\bar{I}_2$ are second autocorrelation signal components. They are expressed by the following formulas:

$$\bar{R}_1 = |S| \cos \theta_1, \quad (24)$$
$$\bar{I}_1 = |S| \sin \theta_1,$$
$$\theta_1 = 2\pi f_d T_1$$
$$\bar{R}_2 = |S| \cos \theta_2, \quad (25)$$
$$\bar{I}_2 = |S| \sin \theta_2,$$
$$\theta_2 = 2\pi f_d T_2$$

The following formula is obtained by substituting formulas (24), (25) into formula (23):

$$\begin{aligned} x_7 &= \bar{R}_1\bar{R}_2 + \bar{I}_1\bar{I}_2 \\ &= |S|^2 (\cos \theta_1 \cos \theta_2 + \sin \theta_1 \sin \theta_2) \\ &= |S|^2 \cos(\theta_1 - \theta_2) \end{aligned} \quad (26)$$

$$\begin{aligned} y_7 &= \bar{I}_1\bar{R}_2 - \bar{R}_1\bar{I}_2 \\ &= |S|^2 (\sin \theta_1 \cos \theta_2 + \cos \theta_1 \sin \theta_2) \\ &= |S|^2 \sin(\theta_1 - \theta_2) \end{aligned} \quad (27)$$

The complex signal of the complex product obtained in this way is supplied to the argument calculator 86 to obtain the argument from the following formula:

$$\begin{aligned} \theta_1 - \theta_2 &= \tan^{-1}(x_7/y_7) \\ &= 2\pi f_d (T_1 - T_2) \\ &= 2\pi f_d \Delta T \end{aligned} \quad (28)$$

Insertion of integrators 88a, 88b consisting of the delay lines 60, the adders 62 and the weighting circuits 64 between the complex multiplier 84 and the argument calculator 86 enables highly accurate measurement free from a noise signal.

The final argument obtained in this way corresponds to a third Doppler signal which is obtained from the two Doppler signal having different repetition periods, and it is possible to obtain the velocity of moving reflective members from this argument.

In formula (28), the repetition period $\Delta T = T_1 - T_2$, which turns out to be the same signal as the Doppler signal obtained when the ultrasonic wave having the repetition period $\Delta T$ is transmitted into the organism to be examined.

Accordingly, for example, if the repetition period $T_1 = 250$ $\mu s$ (the repetition frequency $f_r1 = 4$ KHz) and the repetition period $T_2 = 200$ $\mu s$ (the repetition frequency $f_r2 = 5$ KHz), $\Delta T$ equals 50 $\mu s$ (the repetition frequency $f_r=20$ KHz). As a result, the maximum measurable Doppler frequency in this case is 20 KHz÷2=10 KHz, which is four times the maximum Doppler frequency 2.5 KHz (=5 KHz÷2) obtained when the repetition period is $T_2$.

In this manner, high-speed measurement is enabled by obtaining the conjugate product of autocorrelation signals, and it is possible to convert a Doppler signal to a desired signal without almost any change in the maximum measuring depth by selecting appropriate values for the repetition periods $T_1$ and $T_2$.

Calculation of the complex product of autocorrelation signals will now be explained.

The complex product is obtained by operating the adder-subtracters 82a of the complex multiplier 84 as a subtracter, and the adder subtracter 82b as an adder in the opposite manner to the case of calculating the conjugate product.

The complex product is expressed by the following formula:

$$(\bar{R}_1 + j\bar{I}_1)(\bar{R}_2 + j\bar{I}_2) \quad (29)$$
$$= \bar{R}_1\bar{R}_2 - \bar{I}_1\bar{I}_2 + j(\bar{I}_1\bar{R}_2 + \bar{R}_1\bar{I}_2)$$
$$= x_7 + jy_7$$

The final argument obtained in this way is represented as follows:

$$\theta_1 + \theta_2 = 2\pi f_d(T_1 + T_2) \quad (30)$$

The argument $(\theta_1+\theta_2)$ corresponds to a velocity signal obtained when the ultrasonic wave having a short repetition period, namely, having a low repetition frequency is transmitted. Since the velocity value is enlarged in a predetermined speed range when the Doppler frequency fd is low, as described above, it is easy to detect a low speed.

The velocity signal obtained in this manner is converted to an analog voltage signal by a D/A converter 68, and the resulting analog signal is applied to the CRT display 30 via a switch 70 as a brightness modulation signal, whereby the velocity distribution of the movement is displayed as a picture on the CRT display 30 in either B-mode or M-mode.

According to the second embodiment, the CRT display 30 can selectively display either the ordinary video signal or the Doppler signal, or can display both of these signals simultaneously. That is, either of the pictures can be displayed independently or they can be displayed in the overlapping state.

The Doppler ultrasonic diagnostic apparatus according to the first and second embodiment are adaptable to display in M-mode, two-dimensional step scanning in B-mode, and a moving-target indicator (MTI). In the case of B-mode, it is possible to display the Doppler signal over the tomograph of an organism to be examined.

As described above, according to the present invention, it is possible to obtain the accurate velocity of moving reflective members by transmitting two kinds of ultrasonic waves having different repetition periods into an organism to be examined, and calculating the sum of or the difference between the two velocity signals obtained therefrom, or calculating the conjugate product or the complex product of the two autocorrelation signals obtained therefrom.

Consequently, it is possible to simultaneously display the velocity of blood flow and the velocity distribution of blood flow in addition to the diagnostic information from a conventional diagnostic apparatus which employs the diagnostic echo method. Thus, the present invention provides an ultrasonic diagnostic apparatus which is capable of providing a large amount of practically useful diagnostic information.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. A two-dimensional Doppler ultrasonic blood flow display device of the type wherein a velocity of moving reflective members in an organism to be examined is detected by transmitting ultrasonic waves into said organism and comparing a transmitting signal and a received signal, said device comprising:
   a transmission circuitry means for producing two ultrasonic waves having different repetition periods in the same direction and alternately outputting said two ultrasonic waves;
   a velocity calculator means for calculating the velocities of the moving reflective members from the respective received Doppler signals of said two ultrasonic waves;
   a memory means for storing a first velocity signal obtained by said velocity calculator on the basis of the ultrasonic wave which has been transmitted first in said direction; and
   an adder/subtractor means for calculating the difference between a second velocity signal obtained by said velocity calculator means on the basis of the next consecutive ultrasonic wave transmitted in said direction and said first velocity signal, thereby accurately obtaining the velocity of said moving reflective members.

2. A device according to claim 1, wherein said adder/subtractor means calculates a sum of said second velocity signal and said first velocity signal.

3. A two-dimensional Doppler ultrasonic blood flow display device of the type wherein a velocity of moving reflective members in an organism to be examined is detected by transmitting ultrasonic waves into said organism and comparing a transmitting signal and a receiving signal, said device comprising:
   a transmission circuitry means for producing two ultrasonic waves having different repetition periods in the same direction and for alternately outputting said two ultrasonic waves;
   a complex signal converter means for mixing and detecting a Doppler signal obtained from said organism and a complex reference wave and converting the mixed Doppler signal and complex reference wave to a complex signal;
   an autocorrelator means for calculating the autocorrelation of said complex signal by providing a delay time which is an integer multiple of a transmission repetition period of said two ultrasonic waves;
   a memory means for storing a first autocorrelation signal obtained by said autocorrelator means on the basis of the ultrasonic wave which has been transmitted first in said direction; and
   a velocity processor means for obtaining the velocity of said moving reflective members by calculating the conjugate product of a second autocorrelation signal obtained by said autocorrelator means on the basis of the next consecutive ultrasonic wave transmitted in said direction and said first autocorrelation signal, thereby accurately obtaining the velocity of said moving members.

4. A device according to claim 3, wherein said velocity processor means calculates the complex product of said second autocorrelation signal and said first autocorrelation signal.

* * * * *